(12) United States Patent
Whitekettle et al.

(10) Patent No.: US 7,824,557 B2
(45) Date of Patent: Nov. 2, 2010

(54) METHOD FOR CONTROLLING MICROBIAL BIOFILM IN AQUEOUS SYSTEMS

(75) Inventors: Wilson Kurt Whitekettle, Jamison, PA (US); Gloria Jean Tafel, Doylestown, PA (US); Qing Zhao, Shanghai (CN)

(73) Assignee: General Electric Company, Schenectady, NY (US)

( * ) Notice: Subject to any disclaimer, the term of this patent is extended or adjusted under 35 U.S.C. 154(b) by 425 days.

(21) Appl. No.: 11/835,722

(22) Filed: Aug. 8, 2007

(65) Prior Publication Data

US 2009/0039035 A1    Feb. 12, 2009

(51) Int. Cl.
*C02F 1/50*    (2006.01)

(52) U.S. Cl. .................. 210/755; 210/754; 210/756; 210/759; 210/764; 210/916; 422/28; 422/37; 424/417; 424/450

(58) Field of Classification Search .................. 210/764
See application file for complete search history.

(56) References Cited

U.S. PATENT DOCUMENTS

| | | | |
|---|---|---|---|
| 4,561,981 A * | 12/1985 | Characklis | .................. 210/696 |
| 5,063,213 A | 11/1991 | Whitekettle et al. | |
| 5,081,134 A | 1/1992 | Whitekettle et al. | |
| 5,093,357 A | 3/1992 | Whitekettle et al. | |
| 5,164,096 A * | 11/1992 | Nunn | ......................... 210/754 |
| 5,411,666 A | 5/1995 | Hollis et al. | |
| 5,547,939 A * | 8/1996 | Selsted | ........................ 514/14 |
| 5,789,239 A | 8/1998 | Eyers et al. | |
| 6,267,897 B1 | 7/2001 | Robertson et al. | |
| 6,267,979 B1 | 7/2001 | Raad et al. | |
| 6,498,862 B1 | 12/2002 | Pierson et al. | |
| 6,579,541 B2 * | 6/2003 | Antelman | .................. 424/646 |
| 6,759,040 B1 | 7/2004 | Manyak et al. | |
| 6,811,711 B2 * | 11/2004 | Unhoch et al. | ............... 210/755 |
| 6,998,049 B1 * | 2/2006 | Meyer et al. | ................. 210/632 |

* cited by examiner

*Primary Examiner*—Peter A Hruskoci
(74) *Attorney, Agent, or Firm*—GE Global Patent Operation; Barbara A. Toop; Catherine J. Winter

(57) ABSTRACT

A process has been found which increases the efficiency and effectiveness of introducing antimicrobial compounds into complex biofilm matrices through the use of liposome carriers, thereby removing the biofouling in industrial water bearing systems, including piping, heat exchanges, condensers, filtration systems and fluid storage tanks.

According to one embodiment of the invention, antimicrobial compound containing liposomes are added to water systems prone to biofouling and biofilm formation. The liposomes, being similar in composition to microbial membranes or cells, are readily incorporated into the existing biofilm. Once the antimicrobial compound containing liposomes become entrained with the biofilm matrix, the decomposition or programmed disintegration of the liposome proceeds. Thereafter the biocidal aqueous core is released to react directly with the biofilm encased microorganisms. Upon the death of the organisms, the polysaccharide/protein matrix decomposes and thereby results in reduced fouling of the water bearing system, resulting in increased heat transfer, increased flux, less deposit of colloidal and particulate solids and dissolved organics on the surface of the microfiltration membrane, thereby reducing the frequency and duration of the membrane cleaning and ultimate replacement.

18 Claims, 2 Drawing Sheets

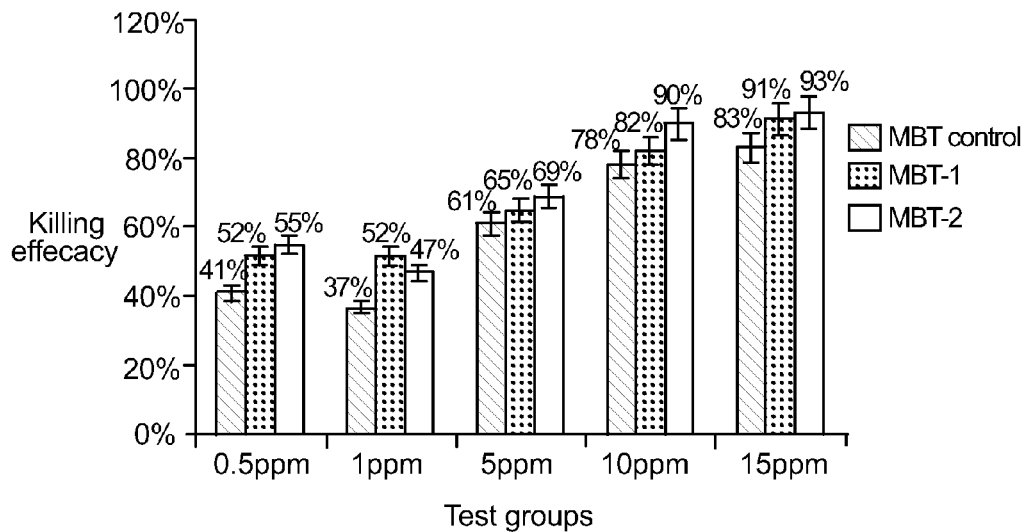
FIG. 1 Liposome/MBT biocidal efficacy on Pseudomonas fluoresens biofilm
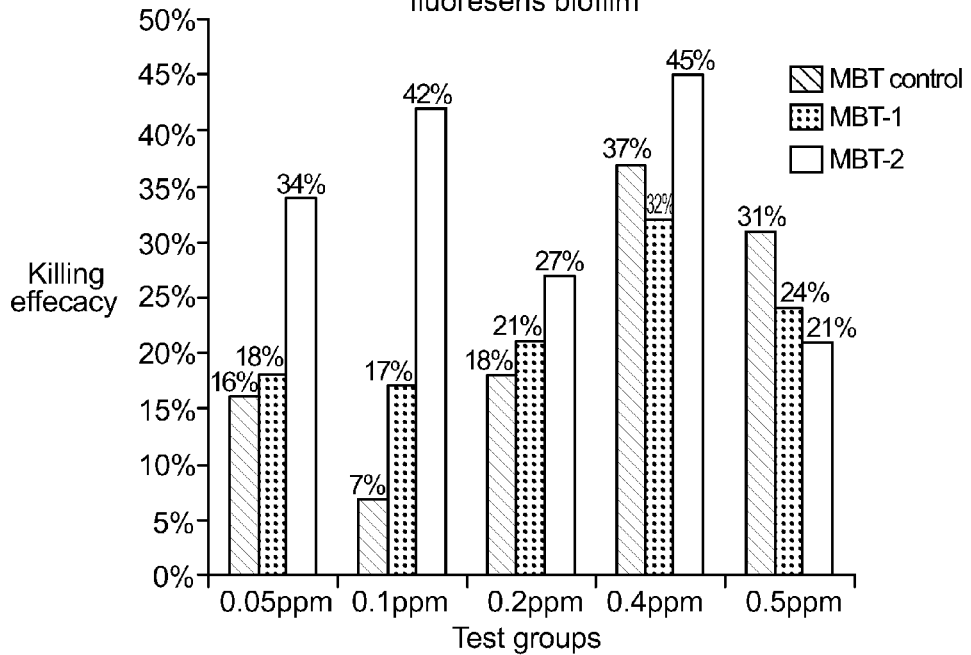
FIG. 2 Liposome/MBT biocidal efficacy on Pseudomonas fluoresens biofilm

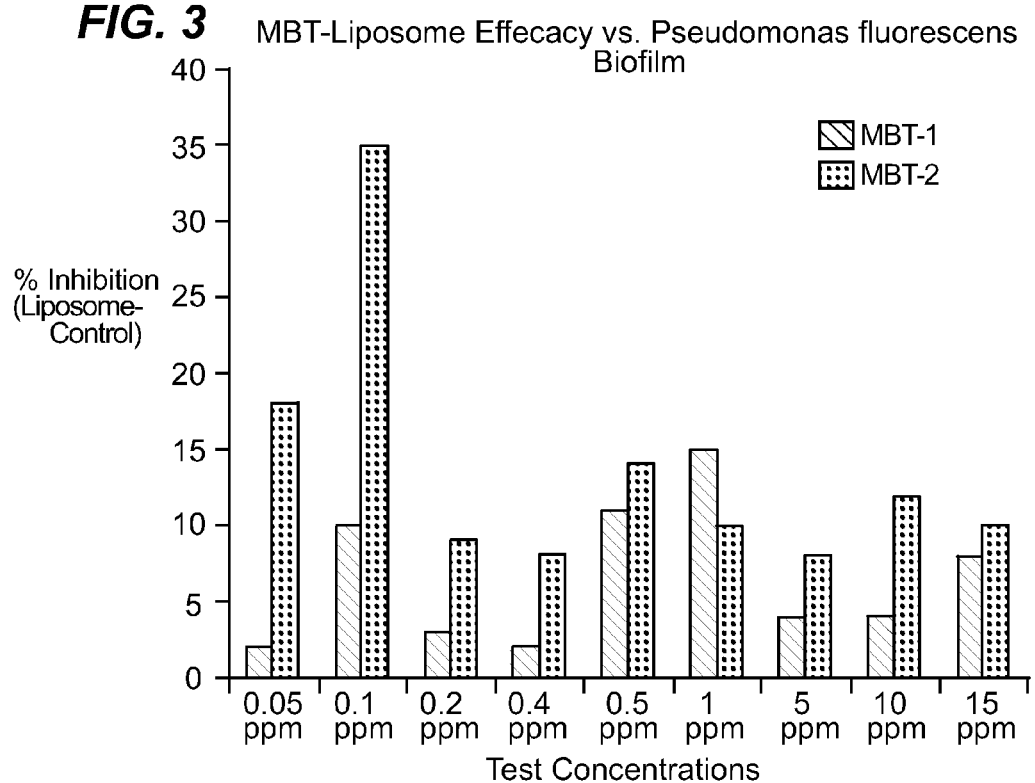
FIG. 3 MBT-Liposome Effecacy vs. Pseudomonas fluorescens Biofilm
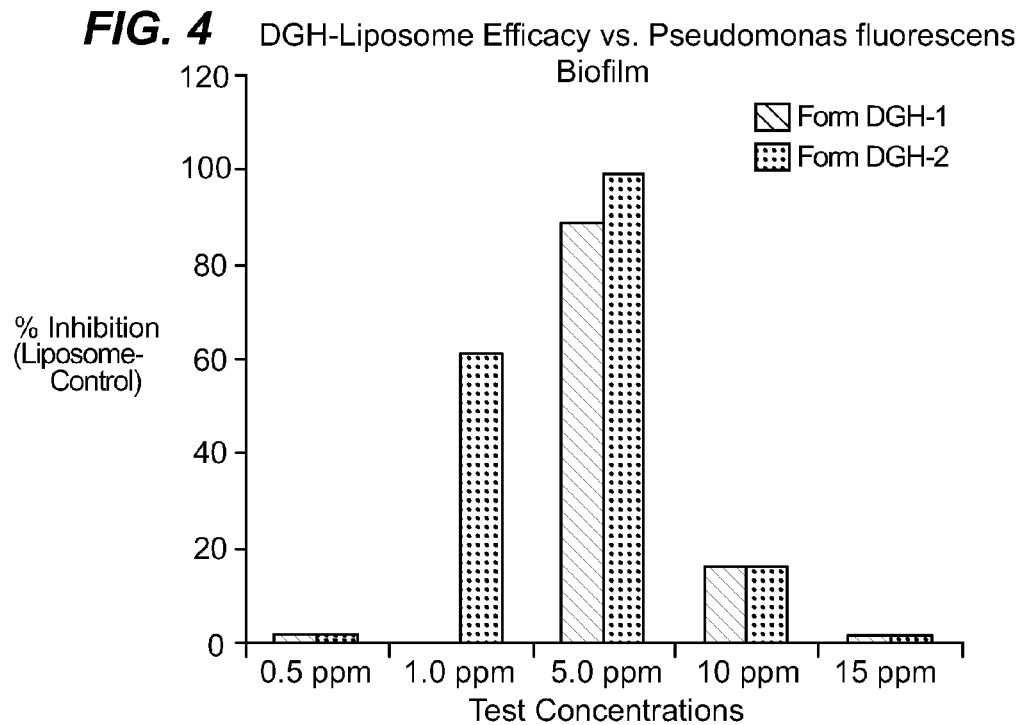
FIG. 4 DGH-Liposome Efficacy vs. Pseudomonas fluorescens Biofilm

METHOD FOR CONTROLLING MICROBIAL BIOFILM IN AQUEOUS SYSTEMS

FIELD OF THE INVENTION

The field of the invention relates to destroying microbial biofilms in aqueous systems. More particularly, the invention relates to the use of antimicrobial or other compounds to destroy microbial biofilm.

BACKGROUND OF THE INVENTION

Many different types of industrial or commercial operations rely on large quantities of water for various reasons, such as for cooling systems, or produce large quantities of wastewater, which need to be treated. These industries include, but are not limited to, agriculture, petroleum, chemical, pharmaceutical, mining, metal plating, textile, brewing, food and beverage processing, and semiconductor industries. Naturally occurring biofilms are continuously produced and often accumulate on numerous structural or equipment surfaces or on natural or biological surfaces. In industrial settings, the presence of these biofilms causes a decrease in the efficiency of industrial machinery, requires increased maintenance and presents potential health hazards. An example is the surfaces of water cooling towers which become increasingly coated with microbially produced biofilm slime which constricts water flow and reduces heat exchange capacity. Specifically, in flowing or stagnant water, biofilms can cause serious problems, including pipeline blockages, corrosion of equipment by growth of underfilm microbes and the growth of potentially harmful pathogenic bacteria. Water cooling tower biofilms may form a harbor or reservoir that perpetuates growth of pathogenic microorganisms such as *Legionella pneumophila*.

Food preparation lines are routinely plagued by biofilm build-up both on the machinery and on the food product where biofilms often include potential pathogens. Industrial biofilms are complex assemblages of insoluble polysaccharide-rich biopolymers, which are produced and elaborated by surface dwelling microorganisms. More particularly, biofilms or microbial slimes are composed of polysaccharides, proteins and lipopolysaccharides extruded from certain microbes that allow them to adhere to solid surfaces in contact with water environments and form persistent colonies of sessile bacteria that thrive within a protective film. The film may allow anaerobic species to grow, producing acidic or corrosive conditions. To control these problems, processes and antimicrobial products are needed to control the formation and growth of biofilms. Control of biofilms involves preventing microbial attachment and/or removing existing biofilms from surfaces. While removal in many contexts is accomplished by short cleansing treatments with highly caustic or oxidizing agents, the most commonly used materials to control biofilms are biocides and dispersants. In U.S. Pat. No. 5,411,666, a method of removing a biofilm or preventing buildup of a biofilm on a solid substrate is taught, that comprises a combination of at least two biologically produced enzymes, such as an acidic or alkaline protease and a glucoamylase or alpha amylase and at least one surfactant. U.S. Pat. No. 6,759,040 teaches a method for preparing biofilm degrading, multiple specificity, hydrolytic enzyme mixtures that are targeted to remove specific biofilms.

U.S. Pat. No. 6,267,897, relates to a method of inhibiting biofilm formation in commercial and industrial water systems by adding one or more plant oils to the system. However, although the biocides are effective in controlling dispersed microorganism suspensions, i.e. planktonic microbes, but biocides do not work well against sessile microbes, the basis of biofilms. This is due to the fact that biocides have difficulty penetrating the polysaccharide/protein slime layers surrounding the microbial cells. Thicker biofilms see little penetration of biocides and poor biocide efficacy is the result. As disclosed in the prior art, one method of trying to better control biofilms has been the addition of dispersants and wetting agents to biocide compositions to enhance biocide efficacy. Biodispersants may operate to keep planktonic microbes sufficiently dispersed that they do not agglomerate or achieve the local densities necessary to initiate the extracellular processes responsible for anchoring to a surface, or initiating film- or colony-forming mechanisms. As components in biocidal treatment formulations, these biodispersants have helped in opening channels in the biofilm to allow better permeability of the toxic agents and to better disperse the microbial aggregates and clumps that have been weakened and released from the surfaces. However, biodispersants have proven to be more effective in preventing initial biofilm formation than in removing existing biofilms. In many cases, the activity of biodispersants has been responsible for only 25 to 30% biomass removal from biofouled surfaces, even when used in conjunction with a biocidal agent.

Therefore, a clear need still exists for an efficient and effective means for penetrating existing biofilms and killing biofilm organisms with a biofilm matrix, decrease the fouling of the microfiltration systems, providing less frequent cleaning and/or replacement and would enhance the overall filtration process.

SUMMARY OF THE INVENTION

A process has been found which increases the efficiency and effectiveness of introducing antimicrobial compounds into complex matrices, through the use of liposome carriers, thereby removing the fouling in industrial water conduit systems, including piping, heat exchangers, condensers, filtration systems and media, and fluid storage tanks.

According to one embodiment of the invention, liposomes containing an antimicrobial agent, such as a hydrophilic biocide, are added to a water system prone to biofouling and biofilm formation. The liposomes, being similar in composition to the microbial surface or to material on which the microbes feed, are readily incorporated into the existing biofilm. Once the liposomes become entrained with the biofilm matrix, digestion, decomposition or programmed disintegration of the liposome proceeds, releasing the antimicrobial agent, or biocidal aqueous core reacts locally with the biofilm-encased microorganisms. Upon the death of the organisms, the polysaccharide/protein matrix cannot be replenished and decomposes and thereby results in reduced bio fouling of the water bearing system. Depending on the particular aqueous system involved, this biofilm removal or destruction therefore results in increased heat transfer (industrial heat exchanger), increased flux (filter or filtration membrane), less deposit of colloidal and particulate solids and dissolved organics on the surface of the microfiltration membrane, thereby reducing the frequency and duration of the membrane cleaning and ultimate replacement, or general reduction of corrosive surface conditions in pipelines, tanks, vessels or other industrial equipment.

The various features of novelty that characterize the invention are pointed out with particularity in the claims annexed to and forming a part of this disclosure. For a better understanding of the invention, its operating advantages and benefits obtained by its uses, reference is made to the accompanying drawings and descriptive matter. The accompanying drawings are intended to show examples of the invention. The drawings are not intended as showing the limits of all of the ways the invention can be made and used. Changes to and substitutions of the various components of the invention can of course be made. The invention resides as well in subcombinations and sub-systems of the elements described, and in methods of using them.

BRIEF DESCRIPTION OF THE DRAWINGS

Refer now to the figures, which are meant to be exemplary and not limiting, and wherein like elements are numbered alike, and not all numbers are repeated in every figure for clarity of the illustration.

FIG. 1 shows the results in graph form of the efficacy of liposome/ethylene bis thiocyanate (MBT) at various concentrations.

FIG. 2 shows the results in graph form of the efficacy of liposome/methylene bis thiocyanate (MBT) at various concentrations.

FIG. 3 shows the results in graph form of the efficacy of liposome/MBT at varying concentrations.

FIG. 4 shows the results in graph form of the efficacy of two decylguanidine hydrochloride (DGH)/liposome formulations at varying concentrations.

DETAILED DESCRIPTION OF THE INVENTION

While the present invention is described with references to illustrative examples and preferred embodiments, various changes or substitutions may be made on these embodiments by those ordinarily skilled in the art pertinent to the present invention with out departing from the technical scope of the present invention. Therefore, the technical scope of the present invention encompasses not only those embodiments described above, but also all that fall within the scope of the appended claims.

Approximating language, as used herein throughout the specification and claims, may be applied to modify any quantitative representation that could permissibly vary without resulting in a change in the basic function to which it is related. Accordingly, a value modified by a term or terms, such as "about", is not limited to the precise value specified. In at least some instances, the approximating language may correspond to the precision of an instrument for measuring the value. Range limitations may be combined and/or interchanged, and such ranges are identified and include all the sub-ranges included herein unless context or language indicates otherwise. Other than in the operating examples or where otherwise indicated, all numbers or expressions referring to quantities of ingredients, reaction conditions and the like, used in the specification and the claims, are to be understood as modified in all instances by the term "about".

As used herein, the terms "comprises," "comprising," "includes," "including," "has," "having" or any other variation thereof, are intended to cover a non-exclusive inclusion. For example, a process, method, article or apparatus that comprises a list of elements is not necessarily limited to only those elements, but may include other elements not expressly listed or inherent to such process, method article or apparatus.

A process has been found which increases the efficiency and effectiveness of introducing antimicrobial compounds into complex matrices through the use of liposome carriers, thereby removing the fouling in industrial water conduit systems, including piping, heat exchangers, condensers, filtration systems and media, and fluid storage tanks.

According to one embodiment of the invention, liposomes containing a biocidal or antimicrobial agent or compound are added to an aqueous system prone to biofouling and biofilm formation. The liposomes, being similar in composition to microbial membranes or cells, are readily incorporated into the existing biofilm. Once the antimicrobial compound-containing liposomes diffuse into, adsorb or otherwise become entrained with the biofilm matrix, the decomposition or programmed disintegration of the liposome proceeds. That is lipid decomposition and biocide release can be programmed to occur by making the lipid matrix sensitive to pH, redox potential, $Ca^{+2}$ concentration, or other changes. Thereafter the biocidal component (which may be concentrated in the aqueous core of the liposome or in the lipid membrane portion of the liposome, is released to react directly with the biofilm-encased microorganisms. Thus, rather than adding a biocide at high levels to the bulk water system, a small quantity of liposome-encased biocide is taken up by the biofilm or by free (planktonic) organisms, and degradation of the liposome releases the biocide locally in or at the target organisms or their film matrix niche. The biocide thus attains a high concentration locally to kill the target organisms, and upon the death of the organisms, the polysaccharide/protein matrix that forms the biofilm cannot be regenerated and decomposes, and thereby results in reduced fouling of the water bearing system, resulting in increased heat transfer, increased flux, less deposit of colloidal and particulate solids and dissolved organics on the surface of the microfiltration membrane, thereby reducing the frequency and duration of the membrane cleaning and ultimate replacement or other benefits.

Liposomes, or lipid bodies, are systems in which lipids are added to an aqueous buffer to form vesicles, structures that enclose a volume. More specifically, liposomes are microscopic vesicles, most commonly composed of phospholipids and water. When properly mixed, the phospholipids arrange themselves into a bilayer or multilayers, very similar to a cell membrane, surrounding an aqueous volume core. Liposomes can be produced to carry various compounds or chemicals within the aqueous core, or the desired compounds can be formulated in a suitable carrier to enter the lipid layer(s). Liposomes can be produced in various sizes and may be manufactured in submicron to multiple micron diameters. The liposomes may be manufactured by several known processes. Such processes include, but are not limited to, controlled evaporation, extrusion, injection, microfluid processors and rotor-stator mixers. Liposomes can be produced in diameters ranging from about 10 nanometers to greater than about 15 micrometers. When produced in sizes from about 100 nanometers to about 2 micrometer sizes the liposomes are very similar in size and composition to most microbial cells. The biocide or antimicrobial compound-containing liposomes should be produced in sizes that mimic bacterial cells, from about 0.05 to about 15μ, or alternately, about 0.1 to 10.0μ.

Effective amounts of the biocide containing liposome is introduced into an aqueous system which is prone to biofouling and biofilm formation, or can be introduced into systems that already exhibit signs of biofouling or biofilm formation. The effective amount will vary according to the antimicrobial compound or biocide, and the aqueous system to which it is added, but one embodiment provides from about 0.01 ppm to about 20 ppm, with an alternative of from about 0.05 to about 15 ppm, alternately from about 0.05 to about 0.5 ppm. The liposomes, being similar in composition to microbial membranes, or cells, are readily incorporated into the existing biofilm and become entrained within the biofilm matrix. Upon the decomposition or programmed disintegration of the liposome, the biocidal compound in the aqueous core or bound in the membrane is released to react directly with the biofilm encased microorganisms. Upon the death of the organisms, the polysaccharide/protein matrix will rapidly decompose, freeing the surface from contaminating microbes. A principal feature of the invention is that the liposomes of the present invention constitute extremely small hydrophobic bodies that may readily survive in and disperse in an aqueous system, yet will adsorb to or penetrate a biofilm and preferentially target or be targeted by the microbes that inhabit, constitute or sustain the biofilm. As such, they deliver a biocidal agent directly to the microbes or biofilm, resulting in effective locally biocidal level of activity, without requiring that the aqueous system as a whole sustain a high dose. Thus, where conventional biofilm treatment may require dosing with a bulk biocidal chemical at a certain level, delivery via liposome may be dosed at levels an order of magnitude or more lower in the aqueous system, yet still achieve, or build up to a level that effectively controls or removes biofilm. Indeed, while the terms "antimicrobial" or "biocidal" have been employed to describe the agent carried by the liposome, these agents need not be the highly bioactive materials normally understood by those terms, but may include a number of relatively harmless materials that become highly effective simply by virtue of their highly localized release. Thus, for example, surfactants or harmless salts, when released locally, may affect the normal action of extracellular colony-forming secretions, and are to be included as antimicrobial or biocidal agents for purposes of the invention, and the same mechanism may be employed to deliver other treatment chemicals to the targeted biofilm sites.

Aqueous systems that can be treated by this method include, but are not limited to, potable and non-potable water distribution systems, cooling towers, boiler systems, showers, aquaria, sprinklers, spas, cleaning baths, air washers, pasteurizers, air conditioners, fluid transporting pipelines, storage tanks, ion exchange resins, food and beverage processing lines, metalworking fluid baths, coal and mineral slurries, metal leaching fluids, wastewater treatment facilities, mollusk control, acid mine drainage, or any application prone to biofouling by microbial species. Application such as oil pipelines, where biofilms form in stagnant or pooled aqueous sumps or lenses along the conduit system, may also be effectively treated.

Additional applications for liposome delivery of a treatment chemical are anti-corrosion treatments for equipment generally, delivery of hormone, vitamin or antioxidant treatments or antibiotic and gene therapies for medical or veterinary purposes, delivery of pesticides for agriculture and commercial home uses, effective formulations of food additives and preservatives, targeted delivery for chemical and biological detection systems, color and flavor enhancement, odor control and aquatic pest management.

A variety of known biocides or antimicrobial compounds can be incorporated into the liposomes. Some examples of antimicrobial compounds that can be used include, but are not limited to, non-oxidizing, oxidizing, biodispersant, and molluscicide antimicrobial compounds, and combinations thereof. More specifically, suitable antimicrobial compounds, include, but are not limited to, 2-bromo-2-nitropropane-1,3-diol, 5-chloro-2-methyl-4-isothiazolin-3-one/2-methyl-4-isothiazolin-3-one, n-alkyldimethylbenzylammonium chloride, 2,2-dibromo-3-nitrilopropionamidemethylene-bis(thiocyanate), dodecylguanidine hydrochloride, glutaraldehyde, 2-(tert-butylamino)-4-chloro-6-(ethylamino)-s-triazine, beta-bromonitrostyrene, tributyltinoxide, n-tributyltetradecyl phosphonium chloride, tetrahydroxymethyl phosphonium chloride, 4,5-dichloro-1,2-dithiol-3-one, sodium dimethyldithiocarbamate, disodium ethylenebisdithiocarbamate, Bis(trichloromethyl) sulfone, 3,5-dimethyl-tetrahydro-2H-1,3,5-thiadiazine-2-thione, 1,2-benzisothiazolin-3-one, decylthioethylamine hydrochloride, copper sulfate, silver nitrate, bromochlorodimethylhydantoin, sodium bromide, dichlorodimethylhydantoin, sodium hypochlorite, hydrogen peroxide, chlorine dioxide, sodium chlorite, bromine chloride, peracetic acid and precursors, sodium trichloroisocyanurate, sodium trichloroisocyanurate, ethylene oxide/propylene oxide copolymers, trichlorohexanoic acid, polysiloxanes, carbosilanes, polyethyleneimine, dibromo, dicyano butane and combinations thereof.

Effective amounts of the biocide incorporated into the liposome would depend on the biocide or agent incorporated therein. However effective amounts include from about 0.05 to about 5 grams biocide active per gram lipid, or alternately about 0.1 to about 2 grams biocide active per gram lipid.

Liposomes of the present invention may be created as multi-layer bodies, in which one or more additional layers are provided to enhance the stability of the liposomes or to effectuate a programmed release of the underlying lipid body and contents. Thus, not unlike the technology used to encapsulate medicines for intracorporal delivery, the additional layers may include a protective layer that is hydrolysed or otherwise breaks down over time to provide a sustained release or longer lifetime of the underlying liposome. Such additional layer may additionally or alternatively include an encapsulating polymer that selectively breaks down when the multi-layer liposome encounters a low-pH environment, like the corrosive high acidity environment that may develop beneath a biofilm. A layer may also be compounded to be vulnerable to sulfur-fixing bacteria, causing the liposome to specifically release its biocide in proximity to these corrosive organisms often present in a waste or pipeline system. Furthermore, several such layers may be employed to assure a sufficient lifetime of the liposome, preferably on the order of several days as well as an ability to target a specific niche or environment in the biofilm. This assures that the liposomes will effectively encounter the target organisms or biofilm colonies and deliver their biocides thereto. The lipid material itself may be treated to provide enhanced resistance to hydrolysis or decay, or the added layers may be formed of various hardenable or cross-linkable oils or polymers.

The invention will now be described with respect to certain examples that are merely representative of the invention and should not be construed as limiting thereof.

EXAMPLE

The invention is illustrated in the following non-limiting examples, which are provided for the purpose of representation, and are not to be construed as limiting the scope of the invention. All parts and percentages in the examples are by weight unless indicated otherwise.

Liposomes (150 nanometers average diameter) were created that incorporated the biocide methylene bis thiocyanate (MBT), a US EPA registered biocide active ingredient. The liposomes were then placed in microtiter plates that had microbial biofilms coating them. The microbe inhibiting efficacy of the MBT-liposomes was then compared with non-liposomal MBT when used at the same MBT concentrations. The liposomes containing MBT penetrated the biofilm and inhibited the biofilm organisms much more effectively than the non-liposomal MBT (control MBT) solution.

Two MBT containing liposomes were created designated MBT-1 (155 nm average diameter) and MBT-2 (137 nm average diameter) in the results.

The results are shown in the FIGS. 1, 2 and 3. The non-liposomal MBT is listed as the MBT Control. It is clear from the figures that both liposomal-MBT formulations had better biofilm killing/removal efficiency than the MBT control in the majority of the liposome concentrations that were tested, the exception being with the highest MBT concentration tested. At the high concentration of MBT (0.5 ppm), the use of a liposome as a carrier for the biocide becomes unnecessary. The liposome carrier is highly effective at delivering biocide to the biofilm at low MBT concentrations, thus providing better biofilm control at much reduced BMT concentrations (reduced toxicity and cost performance).

Two dodecylguanidine hydrochloride (DGH) liposome formulations were also created and designated FORM DGH-1 and FORM DGH-2. These liposome formulations were also evaluated against *Pseudomonas fluorescens* biofilms and compared in efficacy to a non-liposome DGH at the same concentration. These results are shown in FIG. 4. Both of these liposome-DGH formulations showed greater efficacy than the control DGH against the *Pseudomonas* biofilm, particularly in the 0.0 to 10 ppm concentration range.

While the present invention has been described with references to preferred embodiments, various changes or substitutions may be made on these embodiments by those ordinarily skilled in the art pertinent to the present invention without departing from the technical scope of the present invention. Therefore, the technical scope of the present invention encompasses not only those embodiments described above, but also all that fall within the scope of the appended claims.

What is claimed is:

1. A process for preventing the fouling of aqueous systems including a biofilm comprising,
    creating an antimicrobial compound containing liposome having a size of from about 0.05 to about 15μ; and
    adding effective amounts of the antimicrobial compound containing liposome to an aqueous system including a biofilm, wherein the antimicrobial compound containing liposome is incorporated into the biofilm, to kill or remove the biofilm and prevent fouling in the aqueous system.

2. The process according to claim 1 wherein the antimicrobial compound is chosen from the group consisting of non-oxidizing, oxidizing, biodispersant, and molluscicide antimicrobial compounds, and combinations thereof.

3. The process according to claim 1 wherein the antimicrobial compound is chosen from the group consisting of, 2-bromo-2-nitropropane-1,3-diol, 5-chloro-2-methyl-4-isothiazolin-3-one/2-methyl-4-isothiazolin-3-one, n-alkyl-dimethylbenzylammonium chloride, 2,2,dibromo-3-nitrilopropionamidemethylene-bis(thiocyanate), dodecylguanidine hydrochloride, glutaraldehyde, 2-(tert-butylamino)-4-chloro-6-(ethylamino)-s-triazine, beta-bromonitrostyrene, tributyltinoxide, n-tributyltetradecyl phosphonium chloride, tetrahydroxymethyl phosphonium chloride, 4,5,-dichloro-1,2,-dithiol-3-one, sodium dimethyldithiocarbamate, disodium ethylenebisdithiocarbamate, Bis(trichloromethyl)sulfone, 3,5-dimethyl-tetrahydro-2H-1,3,5,-thiadiazine-2-thione, 1,2,-benzisothiazolin-3-one, decylthioethylamine hydrochloride, copper sulfate, silver nitrate, bromochlorodimethylhydantoin, sodium bromide, dichlorodimethylhydantoin, sodium hypochlorite, hydrogen peroxide, Chlorine dioxide, sodium chlorite, bromine chloride, peracetic acid and precursors, sodium trichloroisocyanurate, sodium trichloroisocyanurate, ethylene oxide/propylene oxide copolymers, trichlorohexanoic acid, polysiloxanes, carbosilanes, polyethyleneimine, dibromo, dicyano butane and combinations thereof.

4. The process according to claim 1 wherein the biocide or antimicrobial compound containing liposomes is produced in sizes from about 0.1 to about 10μ.

5. The process according to claim 1 wherein the antimicrobial compound is incorporated into a liposome in an amount of from about 0.05 to about 5.0 grams biocide active per gram lipid.

6. The process according to claim 1 wherein the antimicrobial compound is incorporated into a liposome in an amount of from about 0.1 to about 2.0 grams biocide active per gram lipid.

7. The process according to claim 1 wherein the antimicrobial compound containing liposome is added to an aqueous system in an amount of from about 0.01 ppm to about 20 ppm.

8. The process according to claim 1 wherein the aqueous system is chosen from the group consisting of water distribution systems, cooling towers, boiler systems, showers, aquaria, sprinklers, spas, cleaning baths systems, air washers, pasteurizers, air conditioners, fluid transporting pipelines, storage tanks, ion exchange resins, food and beverage processing lines, metalworking fluid baths, coal and mineral slurries, metal leaching fluids, wastewater treatment facilities, mollusk control, acid mine drainage, or any application prone to biofouling by microbial species.

9. The process according to claim 1 wherein the aqueous system is chosen from the group consisting of anti-corrosion treatments, hormone, vitamin or anti-oxidant treatments, antibiotic and gene therapies, pesticides for agriculture and commercial home uses, food additives and preservatives, chemical and biological detection, color and flavor enhancement, odor control and aquatic pest management.

10. A process for reducing or eliminating the fouling of aqueous systems including a biofilm comprising,
    creating an antimicrobial compound containing liposome having a size of from about 0.05 to about 15μ; and
    adding effective amounts of the antimicrobial compound containing liposome to an aqueous system including a biofilm, wherein the antimicrobial compound containing liposome is incorporated into the biofilm, to kill or remove the biofilm and reduce or eliminate fouling in the aqueous system.

11. The process according to claim 10 wherein the antimicrobial compound is chosen from the group consisting of non-oxidizing, oxidizing, biodispersant, and molluscicide antimicrobial compounds, and combinations thereof.

12. The process according to claim 10 wherein the antimicrobial compound is chosen from the group consisting of, 2-bromo-2-nitropropane-1,3-diol, 5-chloro-2-methyl-4-isothiazolin-3-one/2-methyl-4-isothiazolin-3-one, n-alkyl-dimethylbenzylammonium chloride, 2,2,dibromo-3-nitrilopropionamidemethylene-bis(thiocyanate), dodecylguanidine hydrochloride, glutaraldehyde, 2-(tert-butylamino)-4-chloro-6-(ethylamino)-s-triazine, beta-bromonitrostyrene, tributyltinoxide, n-tributyltetradecyl phosphonium chloride, tetrahydroxymethyl phosphonium chloride, 4,5,-dichloro-1,2,-dithiol-3-one, sodium dimethyldithiocarbamate, disodium ethylenebisdithiocarbamate, Bis(trichloromethyl)sulfone, 3,5-dimethyl-tetrahydro-2H-1,3,5,-thiadiazine-2-thione, 1,2,-benzisothiazolin-3-one, decylthioethylamine hydrochloride, copper sulfate, silver nitrate, bromochlorodimethylhydantoin, sodium bromide, dichlorodimethylhydantoin, sodium hypochlorite, hydrogen peroxide, chlorine dioxide, sodium chlorite, bromine chloride, peracetic acid and precursors, sodium trichloroisocyanurate, sodium trichloroisocyanurate, ethylene oxide/propylene oxide copolymers, trichlorohexanoic acid, polysiloxanes, carbosilanes, polyethyleneimine, dibromo, dicyano butane and combinations thereof.

13. The process according to claim 10 wherein the antimicrobial compound containing liposomes is produced in sizes from about 0.1 to about 10μ.

14. The process according to claim 10 wherein the antimicrobial compound is incorporated into a liposome in an amount of from about 0.05 to about 5.0 grams biocide active per gram liquid.

15. The process according to claim 10 wherein the antimicrobial compound is incorporated into a liposome in an amount of from about 0.1 to about 2.0 grams biocide active per gram liquid.

16. The process according to claim 10 wherein the antimicrobial compound containing liposome is added to an aqueous system in an amount of from about 0.01 ppm to about 20 ppm.

17. The process according to claim 10 wherein the aqueous system is chosen from the group consisting of water distribution systems, cooling towers, boiler systems, showers, aquaria, sprinklers, spas, cleaning baths systems, air washers, pasteurizers, air conditioners, fluid transporting pipelines, storage tanks, ion exchange resins, food and beverage processing lines, metalworking fluid baths, coal and mineral slurries, metal leaching fluids, wastewater treatment facilities, mollusk control, acid mine drainage, or any application prone to biofouling by microbial species.

18. The process according to claim 10 wherein the aqueous system is chosen from the group consisting of anti-corrosion treatments, hormone, vitamin or anti-oxidant treatments, antibiotic and gene therapies, pesticides for agriculture and commercial home uses, food additives and preservatives, chemical and biological detection, color and flavor enhancement, odor control and aquatic pest management.

* * * * *